United States Patent [19]

Aoshiro

[11] 4,216,767
[45] Aug. 12, 1980

[54] ENDOSCOPE WITH CLOSED PRESSURIZED INNER CAVITY

[75] Inventor: Hisatake Aoshiro, Tokyo, Japan

[73] Assignee: Machida Endoscope Co., Ltd., Tokyo, Japan

[21] Appl. No.: 877,899

[22] Filed: Feb. 15, 1978

[30] Foreign Application Priority Data

Feb. 21, 1977 [JP] Japan .................................. 52/19060

[51] Int. Cl.² .............................................. A61B 1/06
[52] U.S. Cl. ......................................... 128/6; 350/61; 422/33; 134/171; 134/94
[58] Field of Search .............. 128/4, 5, 6, 7, 8, 303.15, 128/485; 422/28, 29, 30, 31, 32, 33, 34, 35, 36, 37; 134/94, 102, 170, 171, 166 R, 166 C; 350/61, 62, 63, 64, 65, 66, 67

[56] References Cited

U.S. PATENT DOCUMENTS

| 1,335,073 | 3/1920 | Osborn | 73/45.5 |
|---|---|---|---|
| 1,345,406 | 7/1920 | Rimmer | 128/7 |
| 2,667,813 | 2/1954 | MacGill | 350/67 |
| 2,761,311 | 9/1956 | Baker | 73/46 |
| 3,057,345 | 10/1962 | Ferris et al. | 128/8 |
| 3,081,767 | 3/1963 | Hett | 128/6 |
| 3,417,745 | 12/1968 | Sheldon | 128/6 |
| 3,425,419 | 2/1969 | Dato | 128/303.1 |
| 3,726,272 | 4/1973 | Fukami et al. | 128/6 |
| 3,963,438 | 6/1976 | Banez | 422/31 |
| 3,995,934 | 12/1976 | Nath | 350/96.26 |
| 4,064,886 | 12/1977 | Heckele | 134/171 |

FOREIGN PATENT DOCUMENTS 2062178  6/1972  Fed. Rep. of Germany .............. 128/4

*Primary Examiner*—Robert W. Michell
*Assistant Examiner*—Arthur S. Rose
*Attorney, Agent, or Firm*—Peter L. Berger

[57] ABSTRACT

An endoscope comprising one or plural fluid inlets at the grip end of the endoscope or at the feeding pipe which contains an air-feeding pipe and a light-transmitting optical fiber.

For washing and sterilization of endoscope which does not have a water-proof structure, compressed air or liquid is infused through the fluid inlet, raising the inner pressure of the endoscope to prevent the permeation of the cleanser and disinfectant into the innerside of the endoscope.

For washing and sterilization of an endoscope which has a water-proof structure, the compressed air or the liquid is infused through the fluid inlet to detect a pin hole on the surface of a flexible sheath.

6 Claims, 1 Drawing Figure

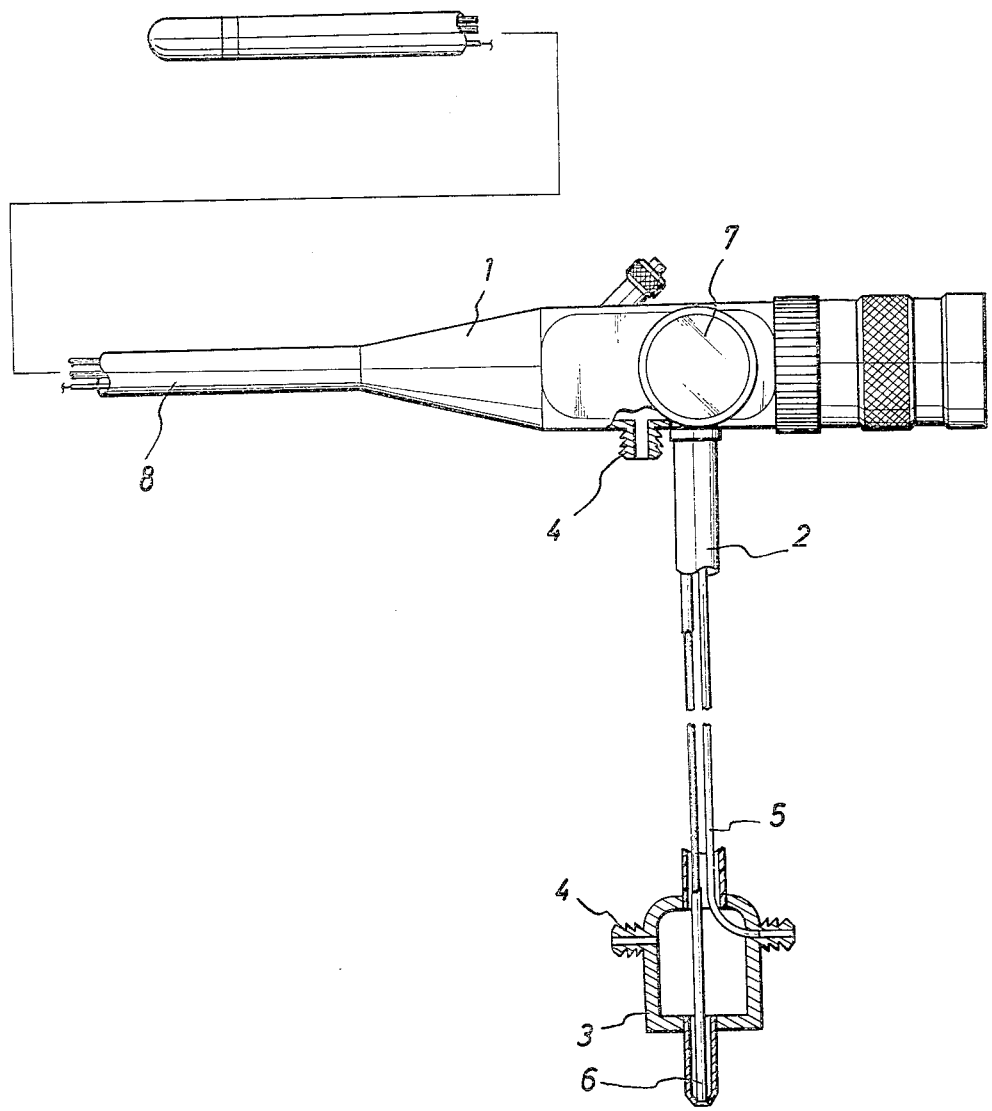

ENDOSCOPE WITH CLOSED PRESSURIZED INNER CAVITY

BACKGROUND OF THE INVENTION

The present invention relates to an endoscope comprising one or plural fluid inlets at the grip end of the endoscope or at the feeding pipe.

The inner portion and the outer surface of the endoscope must be cleanly washed and sterilized after use. The apical portion of the endoscope and a flexible sheath can easily be made water-proof, but a water-proof structure for the grip end is very difficult to achieve. A water-proof structure for the rotating portion such as an angle deflector dial is very hard to achieve.

If the water-proof structure of such a portion is not complete, the cleanser and disinfectant permeate into the inner portion of the endoscope from there. In case of washing and sterilization of the endoscope which has water-proof structure, the permeation of the body fluid or the cleanser and disinfectant from a pin hole or a crack sometimes occurs. The detection of the pin hole is difficult and is an important problem for endoscopes, but the prior art relating to the problem has not yet solved these difficulties

SUMMARY OF THE INVENTION

One or plural fluid inlet are provided at the grip end of the endoscope or at the feeding pipe which contains the air-feeding pipe and the light-transmitting optical fiber.

The first object of the present invention is to provide an endoscope which prevents the permeation of the cleanser and disinfectant to the inner surface thereof, in case the endoscope does not have a water-proof structure.

The second object of the present invention is to provide an endoscope by which a pin hole or a crack on the flexible sheath can easily be detected, in case the endoscope has water-proof structure.

The third object of the present invention is to provide an endoscope which prevents the permeation of the body fluid, in case the endoscope is inserted into the body cavity.

The fourth object of the present invention is to provide an endoscope which prevents the permeation of the body fluid by balancing the pressure of the body cavity against that of the inner portion of the endoscope, in case the endoscope is inserted into the body cavity which is inflated by the air from the air-feeding pipe.

BRIEF DESCRIPTION OF THE DRAWING

The single FIGURE is the partly diagrammatic sectional view of an endoscope embodying the invention.

DETAILED DESCRIPTION OF PREFERRED EMBODIMENT

In the FIGURE, numeral 1 indicates a grip end of an endoscope, numeral 2 indicates a feeding pipe which contains an air-feeding pipe 5 and a light-transmitting optical fiber 6, numeral 3 indicates a connector of the feeding pipe 2, numeral 4 indicates a fluid inlet, numeral 7 indicates an angle deflector dial, numeral 8 indicates a flexible sheath.

The fluid inlet 4 is provided on the surface of the grip end 1 of the endoscope or on the surface or the connector 3 of the feeding pipe 2 which contains an air-feeding pipe 5 and a light-transmitting optical fiber 6. The inner portion of the endoscope communicates with the fluid inlet 4, and the compressed air and the liquid are infused through the fluid inlet 4. The fluid inlet 4 is so shaped as to be easily connected with the other instruments.

By the present invention, the permeation of the cleanser and disinfectant can be prevented through utilizing the fluid inlet for infusing compressed air and liquid, even if the endoscope does not have a water-proof structure at the rotating portion of the angle deflector dial. A pin hole or a crack can be detected by infusing compressed air or liquid through the fluid inlet, if the endoscope has water-proof structure. Permeation of the body fluid into the inner portion of the endoscope can be prevented by balancing the pressure of the body cavity against that of the inner portion of the endoscope, in case the endoscope is inserted into a body cavity which is inflated by the air from the air-feeding pipe.

What is claimed is:

1. An endoscope comprising a grip end, an elongated sheath adapted to fit into a body orifice having a distal end and a proximal end, a fiber optic bundle extending from said proximal end to said distal end of said sheath, said grip end connected with said sheath and said sheath terminating in an examining end, said endoscope including said sheath having a closed inner cavity portion, the portions of said endoscope forming the walls of said closed cavity being non-expandable, said cavity extending along a major portion of said sheath, said sheath being flexible gas inlet means communicating with said closed inner cavity portion of said endoscope, a source of pressurized gas connected to said gas inlet means to introduce pressurized gas into said closed inner cavity portion to be contained therein coupling means for enabling repeated connection between said source of pressurized gas and the gas inlet means for repeatedly pressurizing the inner cavity portion, whereby said pressurized gas prevents cleansing liquid on the outside of said endoscope from permeating said sheath and highlights pinholes in said sheath by the production of gas bubbles thereat.

2. An invention as claimed in claim 1, wherein said gas inlet means is connected at said grip end to be in gas communication with the closed inner cavity.

3. An invention as claimed in claim 2, wherein said grip end comprises said gas inlet means, said gas inlet means comprising a plurality of gas inlets.

4. An invention as claimed in claim 1, wherein said gas inlet means comprises a plurality of said gas inlet couplings.

5. An invention as claimed in claim 1, wherein said source of pressurized gas comprises a source of pressurized air.

6. An invention as claimed in claim 1, wherein said gas inlet means is formed in said grip end.

* * * * *

REEXAMINATION CERTIFICATE (151st)

United States Patent [19]

Aoshiro

[11] B1 4,216,767

[45] Certificate Issued    Dec. 20, 1983

[54] ENDOSCOPE WITH CLOSED PRESSURIZED INNER CAVITY

[75] Inventor: Hisatake Aoshiro, Tokyo, Japan

[73] Assignee: Machida Endoscope Co., Ltd., Tokyo, Japan

Reexamination Request:
No. 90/000,201, May 18, 1982

Reexamination Certificate for:
Patent No.: 4,216,767
Issued: Aug. 12, 1980
Appl. No.: 877,899
Filed: Feb. 15, 1978

[30] Foreign Application Priority Data

Feb. 21, 1977 [JP] Japan .................................. 52-19060

[51] Int. Cl.³ .............................................. A61B 1/06
[52] U.S. Cl. .......................................... 128/6; 350/61; 422/33; 134/171; 134/94
[58] Field of Search ........................... 128/4, 5, 6, 7, 8

[56] References Cited

U.S. PATENT DOCUMENTS

| | | | |
|---|---|---|---|
| 3,070,993 | 1/1963 | Rowell et al. | 73/49.5 |
| 3,381,524 | 5/1968 | Dornbush et al. | 73/45.5 |
| 3,889,662 | 6/1975 | Mitsui | 128/6 |
| 4,076,018 | 2/1978 | Heckele | 128/6 |

FOREIGN PATENT DOCUMENTS

| | | | |
|---|---|---|---|
| 1964496 | 7/1971 | Fed. Rep. of Germany | 128/4 |
| 2062178 | 6/1972 | Fed. Rep. of Germany | 128/4 |

*Primary Examiner*—Lee S. Cohen

[57] ABSTRACT

An endoscope comprising one or plural fluid inlets at the grip end of the endoscope or at the feeding pipe which contains an air-feeding pipe and a light-transmitting optical fiber.

For washing and sterilization of endoscope which does not have a water-proof structure, compressed air or liquid is infused through the fluid inlet, raising the inner pressure of the endoscope to prevent the permeation of the cleanser and disinfectant into the innerside of the endoscope.

For washing and sterilization of an endoscope which has a water-proof structure, the compressed air or the liquid is infused through the fluid inlet to detect a pin hole on the surface of a flexible sheath.

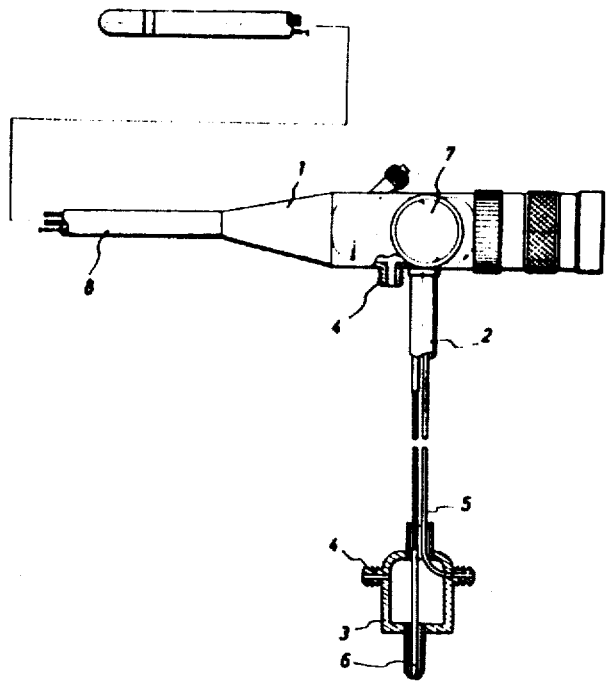

REEXAMINATION CERTIFICATE ISSUED UNDER 35 U.S.C. 307.

ENDOSCOPE WITH CLOSED PRESSURIZED INNER CAVITY

THE PATENT IS HEREBY AMENDED AS INDICATED BELOW.

AS A RESULT OF REEXAMINATION, IT HAS BEEN DETERMINED THAT:

Claims 1-6 having been finally determined to be unpatentable, are cancelled.